United States Patent [19]

Pequegnat

[11] 4,164,199
[45] Aug. 14, 1979

[54] BENTHIC AQUATIC BIOTAL MONITOR

[75] Inventor: Willis E. Pequegnat, College Station, Tex.

[73] Assignee: TerEco Corporation, College Station, Tex.

[21] Appl. No.: 826,052

[22] Filed: Aug. 19, 1977

[51] Int. Cl.² .................... A01K 61/00; A01K 69/04
[52] U.S. Cl. ........................................ 119/2; 119/3; 43/7
[58] Field of Search .............. 119/2, 3; 43/7, 100, 43/101, 102, 103, 104, 105

[56] References Cited
U.S. PATENT DOCUMENTS

| | | | |
|---|---|---|---|
| 721,913 | 3/1903 | Palmer | 43/100 |
| 731,398 | 6/1903 | Watson | 43/100 |
| 1,223,851 | 4/1917 | Carter | 43/105 |
| 1,903,276 | 3/1933 | Yanga | 43/100 |
| 2,163,973 | 6/1939 | Benca et al. | 43/100 |
| 2,921,397 | 1/1960 | Luthi | 43/7 |
| 3,337,982 | 8/1967 | Sajulan | 43/65 |
| 3,795,073 | 3/1974 | Olsen | 43/105 |
| 3,821,861 | 7/1974 | Jalbert | 43/65 |

*Primary Examiner*—Hugh R. Chamblee
*Attorney, Agent, or Firm*—Richards, Harris & Medlock

[57] ABSTRACT

The specification discloses a benthic aquatic biotal monitor for monitoring the chronic impact of pollution, such as industrial and municipal wastes, of aquatic environments upon in situ samples of benthos. The monitor includes a base portion including containers for retaining benthic sample and having a horizontal permeable bottom wall and water permeable vertical side walls. A water permeable mesh is attached to and extends above the base portion to form a conical-shaped enclosure decreasing in cross-sectional area from one end to the other end. The larger end of the conical-shaped enclosure is secured to the base portion and opens thereinto. The smaller end of the conical-shaped portion is closed. The conical-shaped enclosure and the base portion include apertures therethrough with dimensions for retaining benthic samples while permitting the free exchange of ambient water between the outside of the conical-shaped enclosure and the inside of the conical-shaped enclosure to monitor the impact of changing aquatic environments on the benthic sample.

17 Claims, 10 Drawing Figures

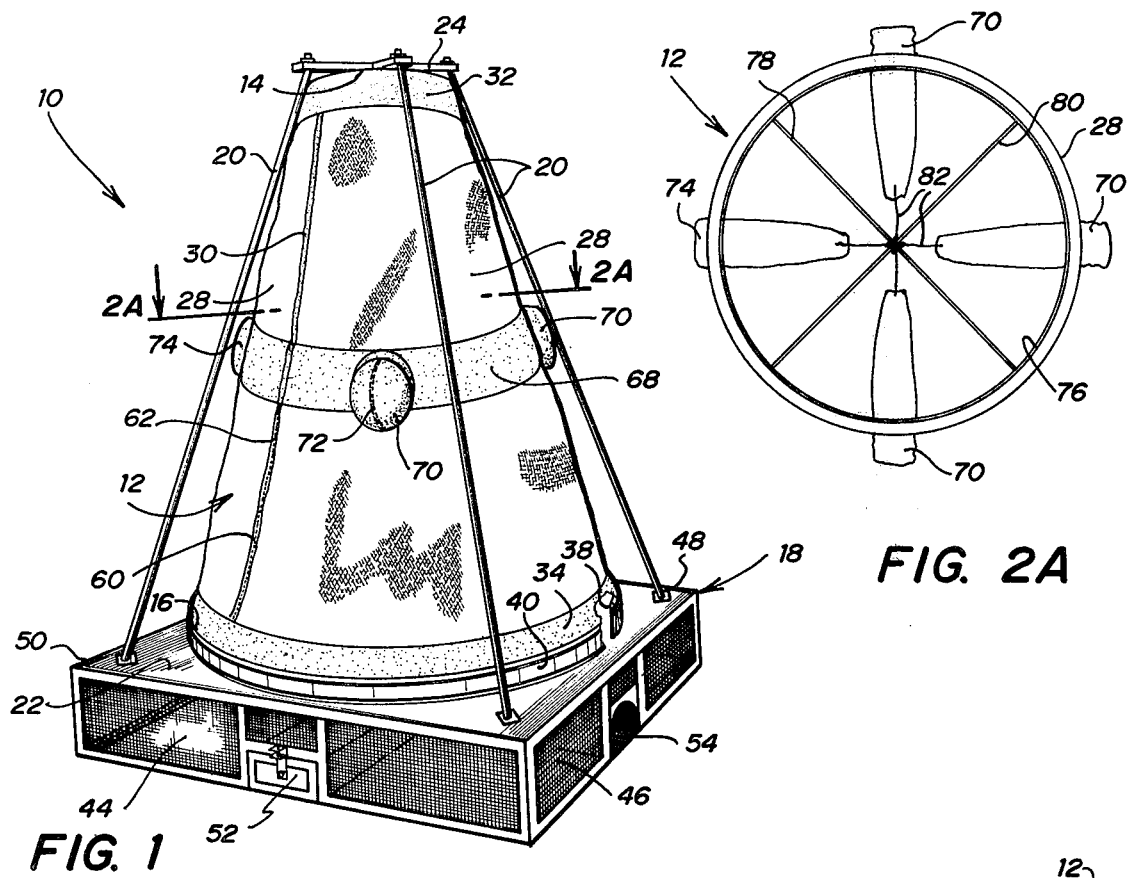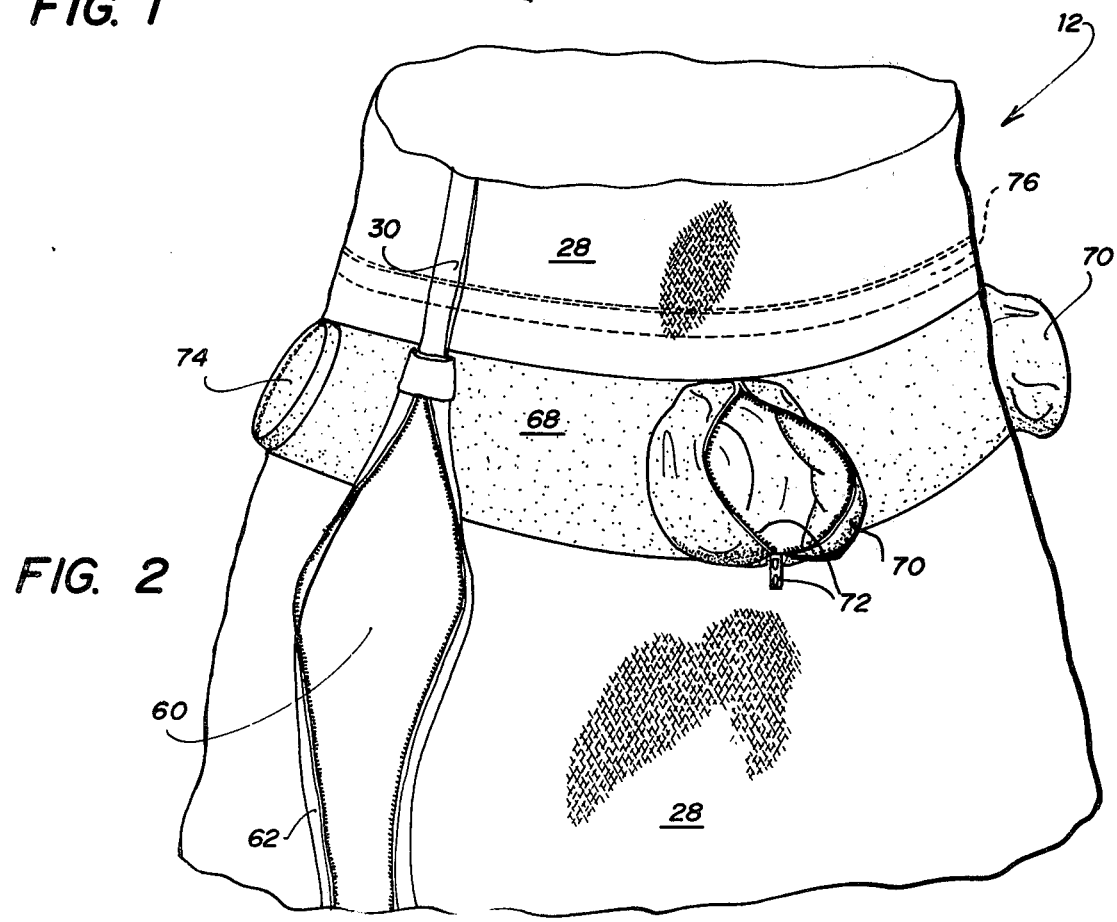

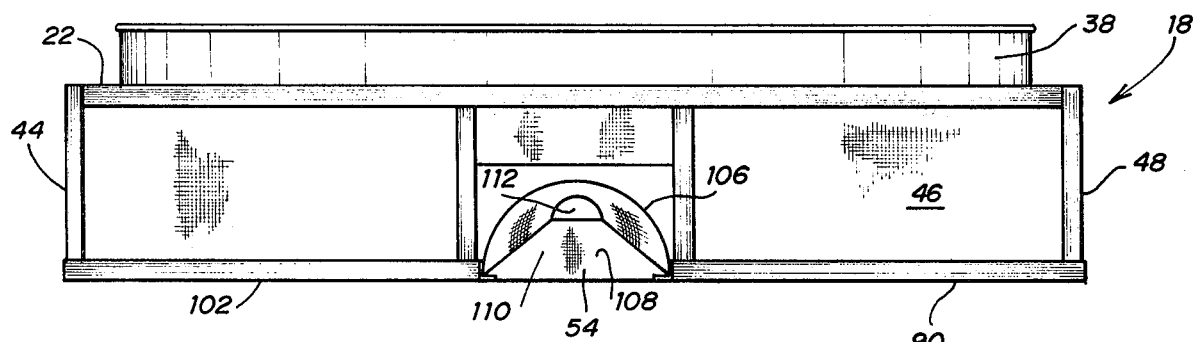
FIG. 5
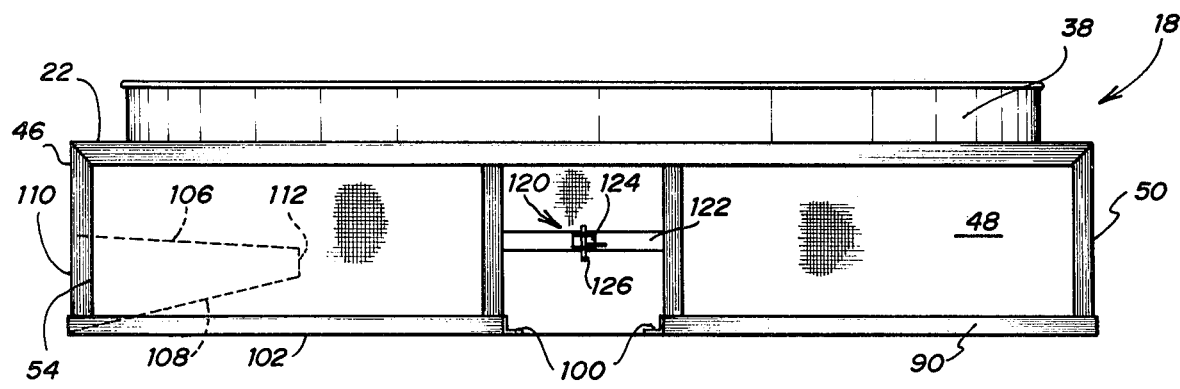
FIG. 6
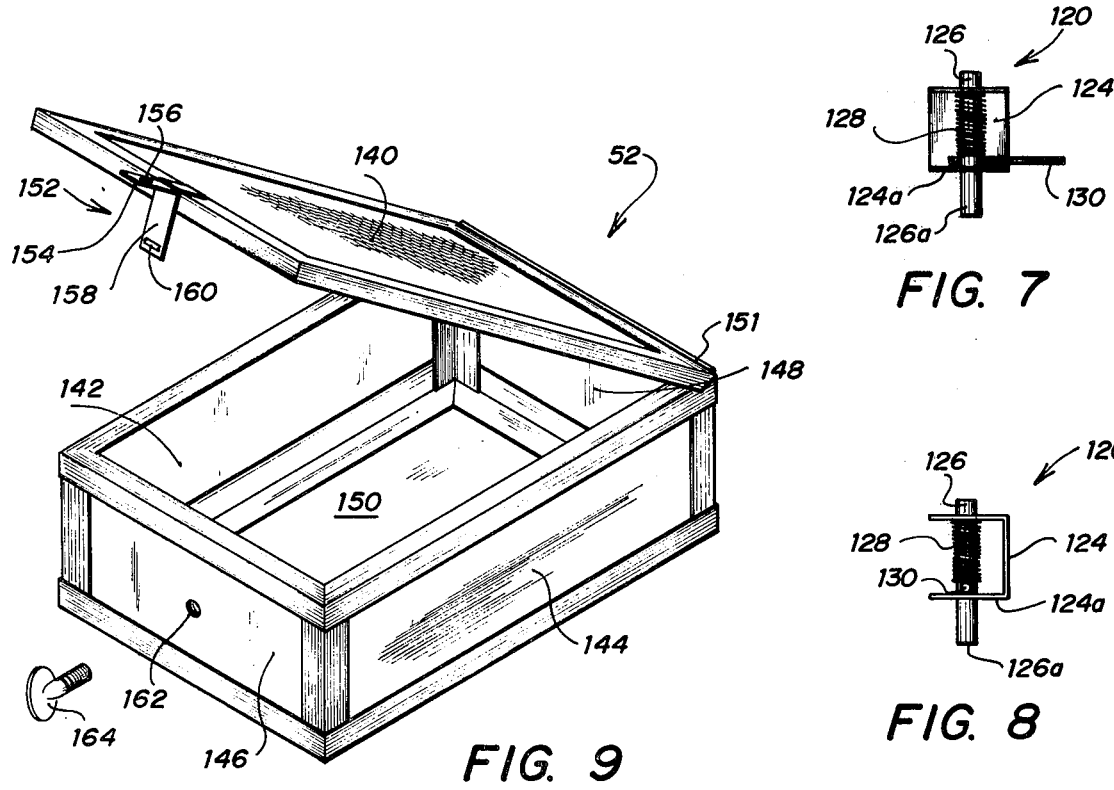
FIG. 9
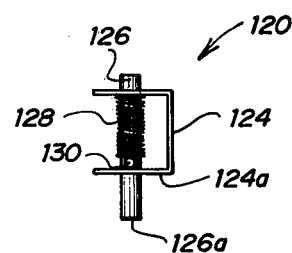
FIG. 7
FIG. 8

BENTHIC AQUATIC BIOTAL MONITOR

FIELD OF THE INVENTION

This invention relates to monitoring devices, and more particularly to a benthic aquatic biotal monitoring device for detecting chronic impacts of pollution of aquatic environments upon in situ benthic samples.

THE PRIOR ART

The quality of our environment and in particular, the quality of the oceans of the world has become an important issue to governments, private industry and individuals. One of the difficult problems facing governments and industry is the disposal of municipal and industrial wastes or dredge material into bodies of water. Determining whether or not waste substances or complexes of substances elicit chronic or other deteriorative responses in the organisms found in these bodies of water is necessary to establish and enforce environmental standards.

It is often thought that the chronic responses to environmental pollution may be more serious than immediate and often more easily determinable acute effects to the environment. To determine these chronic responses, scientists have heretofore used plant and animal samples to test regions of water to detect the presence of pollutants and to determine the pollutants' affect on the samples under observation. In the course of such scientific investigation, ocean monitoring devices are utilized to retain a sample under study and to collect organisms that live in the surrounding environment under study.

It is not particularly difficult to detect the acute impacts of pollution of aquatic environments upon plant and animal, hereinafter referred to as biota, components of the environment. Acute effects develop quickly and therefore do not ordinarily require special monitoring devices for retaining organisms which quickly develop reaction to the pollutants. The detection of chronic impacts of pollution of aquatic environments upon the biotal samples, and in particular, to a benthic sample of organisms that live on or in the bottom of bodies of water, however, requires the same sample to be continuously exposed to the pollutants over extended periods of time in order for a meaningful investigation to be conducted.

A problem in discerning chronic responses results when such monitoring is done at sea, since it is difficult to demonstrate that the organisms sampled were actually exposed to the waste substances. Although laboratory studies can eliminate this problem, laboratory studies are less satisfactory because the species of benthos native to the impacted site may not be adaptable to laboratory conditions. It is also difficult to adjust laboratory levels of impacting substances to those levels occurring in the field.

As a consequence, field studies are superior if a specific sample of benthos can be exposed to the environmental impact and continuously monitored in the field until sufficient time has elapsed for the chronic effect to develop. It is also desirable to collect benthic samples from the impacted environment while the chronic effect may be developing. These chronic effects may take from about four to thirty days to develop.

Previously developed monitoring devices have retained organisms in cage-like structures, but such devices have heretofore not permitted the monitoring of chronic impacts. Prior devices have been designed for environmental studies which utilize impervious enclosure walls designed to keep ambient water out of contact with the benthic sample. Such prior devices have not thus provided a monitor which can retain a benthic sample for extended periods of time while exposing the benthic sample to continuously changing aquatic environments to monitor the chronic impact of benthic pollution.

A need has thus arisen for a benthic aquatic biotal monitoring device which will retain a benthic sample for extended periods of time and expose the sample to continuously changing aquatic environments to enable in situ bioassay studies of various environmental biological effects on the zoobenthos of an area to be studied. Moreover, a need has arisen for a benthic monitoring device that will permit the detection of chronic impacts of pollution of aquatic environments upon a benthic sample, which can be identified both before and after being exposed to the pollutant. Furthermore, a need has arisen for a benthic monitoring device that will collect benthos and free swimming pelagic or demersal species from the surrounding environment for monitoring the effect of exposure to aquatic pollution.

SUMMARY OF THE INVENTION

In accordance with the present invention, a benthic aquatic biotal monitor is presented which will enable the detection of chronic impacts of varying pollution of benthic aquatic environments upon a benthic sample. The monitor permits a sample of benthos to be continuously exposed to ambient water to conduct in situ bioassay studies of various environmental biological effects on the zoobenthos of an area.

In accordance with the present invention, a benthic monitoring device for monitoring in situ samples of benthos in a body of water includes a base portion including containers for retaining benthic samples and having a horizontal water permeable bottom wall and water permeable vertical side walls. A water permeable mesh attached to and extending above the base portion forms a conical-shaped enclosure decreasing in cross-sectional area from one end to the other end. The larger end of the conical-shaped enclosure is secured to the base portion and opens thereinto. The smaller end of the conical-shaped enclosure is closed. The conical-shaped enclosure and the base portion include apertures therethrough with dimensions for retaining benthic samples while permitting the free exchange of ambient water between the outside of the conical-shaped enclosure and the inside of the conical-shaped enclosure to monitor the impact of changing aquatic environments on the benthic sample.

In accordance with another aspect of the present invention, a benthic monitoring device for monitoring in situ samples of benthos in a body of water includes a base portion having water permeable vertical side walls and horizontal top and bottom walls. The vertical side walls include apertures for receiving containers for retaining benthic samples. At least one of the vertical side walls includes an entry passage for allowing benthic organisms found in ambient water outside of the monitoring device to enter the base portion. A water permeable mesh is attached to and extends above the base portion to form a conical-shaped enclosure decreasing in cross-sectional area from one end to the other end. The larger end of the enclosure is secured to the base portion and opens thereinto. The smaller end of the enclosure is closed. The conical-shaped enclosure includes containers for retaining benthic samples, and is supported above the base portion. The monitor further includes structure for attaching the conical-shaped enclosure to the base portion. The conical-shaped enclosure and the base portion include apertures therethrough with dimensions for retaining benthic samples therein, while permitting the free exchange of ambient water between the outside of said conical-shaped enclosure and the inside of said conical-shaped enclosure to thereby expose the samples of benthos to aquatic pollution within the body of water to monitor the impact of changing aquatic environments on the benthic samples.

DESCRIPTION OF THE DRAWINGS

For a more complete understanding of the present invention and for further objects and advantages thereof, reference is now made to the following detailed description taken in conjunction with the accompanying drawings, in which:

FIG. 1 is a perspective view of the benthic aquatic biotal monitoring device of the present invention;

FIG. 2 is a perspective view of the pelagic compartments, access port and the trap of the conical-shaped enclosure of the monitoring device shown in FIG. 1;

FIG. 2A is a sectional view taken generally along sectional lines 2A—2A of FIG. 1 illustrating the pelagic compartments and trap supporting structure of the conical-shaped enclosure;

FIG. 5 is a side elevational view of the base portion of the monitoring device;

FIG. 6 is a front elevational view of the base portion of the monitoring device;

FIG. 7 is a front elevational view of a receptacle spring latch;

FIG. 8 is a side elevational view of the receptacle spring latch shown in FIG. 7; and FIG. 9 is a perspective view of a base portion receptacle.

DESCRIPTION OF THE PREFERRED EMBODIMENT

Figure 3:
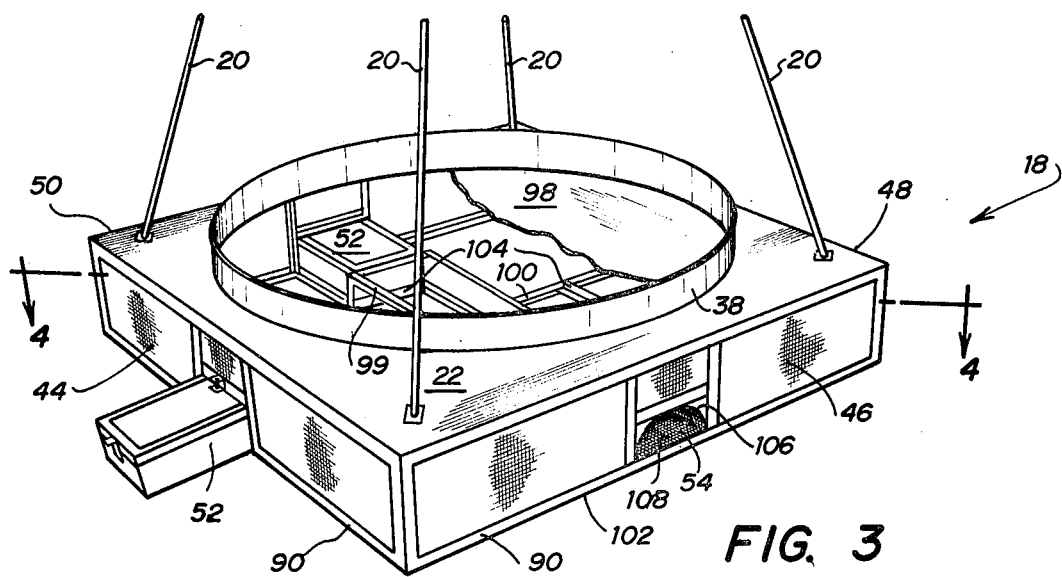
FIG. 3 is a perspective view of the base portion of the monitoring device shown in FIG. 1.

FIG. 1 illustrates the benthic aquatic biotal monitor of the present invention and is identified generally by the numeral 10. The monitor 10 includes a conical-shaped enclosure generally identified by the numeral 12, Which decreases in cross-sectional area from its upper end 14 to its lower end 16 which is larger in area than the upper end 14. The enclosure 12 is secured to a base portion generally identified by the numeral 18, such that the lower end 16 of enclosure 12 opens into the base portion 18. The conical-shaped enclosure 12 is supported above base portion 18 using supporting rods 20. Supporting rods 20 extend from upper surface 22 of the base portion 18 to a top mounting plate 24. Top mounting plate 24 functions to provide a surface for attachment for the upper end 14 of conical-shaped enclosure 12, and provides a point of attachment for a cable (not shown) used to lower and raise the monitor 10 between a ship deck and the sea floor.

In the preferred embodiment, the height of the conical-shaped enclsoure 12 is approximately five feet. The lower end 14 of the enclosure 12 has a diameter of approximately four feet. The dimensions of the base portion 18 of the monitor 10 are approximately four and one-half feet by four and one-half feet by fourteen inches.

The conical-shaped enclosure 12 comprises a water permeable mesh to permit ambient water carrying deleterious substances to circulate freely into and out of the interior of enclosure 12, such that the benthic sample contained therein is exposed to the ambient waters. An essential feature of the present monitor 10 is that the enclosure 12 permits ambient water, dissolved substances and suspended fine particulate matter to freely circulate through the enclosure 12 thereby exposing the benthic samples to the ambient environment to enable the studying of the effect of chronic pollution on zoobenthos of an area. Enclosure 12 includes trapezoidal-shaped wall sections 28, which comprise water permeable mesh. Wall sections 28 may comprise, for example, a netting composed of a non-toxic synthetic fiber such as nylon, which is permeable to water and dissolved material, but which is impervious to benthos of a predetermined size. The mesh size of wall sections 28 is dependant upon the size of the benthos being monitored, but can include apertures of approximately 2 millimeters in size. The netting may comprise, for example, 2200 NYTEX nylon fabric. The trapezoidal-shaped wall sections 28 of the enclosure 12 are joined together by a nylon webbing 30 extending from the upper end 14 to the lower end 16 of the enclosure 12. Enclosure 12 is provided with an upper mounting collar 32 at the upper end 14 and a lower mounting collar 34 at the lower end 16. Collars 32 and 34 are integral with wall portions 28 of enclosure 12 and are circumferentially attached to the upper and lower ends 14 and 16. Collars 32 and 34 are composed of a nylon webbing to provide added strength to the enclosure 12.

The lower end 16 of enclosure 12 is attached at collar 34 to a circular extension 38 mounted to upper surface 22 of the base 18. The collar 34 is affixed to the circular extension 38 using a mounting ring 40. This connection provides for a unitary structure between the enclosure 12 and the base portion 18 of the monitor 10 to allow ambient water and the benthic samples contained therein to freely move between the base portion 18 and enclosure 12.

Base portion 18 includes vertical side walls 44, 46, 48 and 50, which may comprise for example, eight mesh stainless steel wire. Vertical side wall 44 includes a removable receptacle 52 for retaining benthic samples to be exposed to the aquatic environment. Vertical side wall 46 includes a trap 54 that will permit entry into and retention of indigenous species, small crustaceans and demersal fishes, within the interior of the monitor 10. The construction and use of receptacle 52 and trap 54 will be described with reference to FIGS. 5, 6 and 7.

Referring simultaneously to FIGS. 1 and 2, the enclosure 12 includes a zippered access port 60 having a zipper 62. Access port 60 is shown in the open position in FIG. 2. Access port 60 furnishes an entrance necessary to load the interior of monitor 10 with desired specimens and also provides an opening by which exposed samples can be removed from the monitor 10. Although one access port 60 is illustrated, additional ports can be utilized positioned circumferentially around the enclosure 12.

Referring simultaneously to FIGS. 2 and 2A, centrally disposed on the enclosure 12 is a reinforced canvas web 68 including pelagic compartments 70 having a zipper 72 and a funnel trap 74. Pelagic compartments 70 and trap 74 are conical in shape, extend inwardly towards the center of enclosure 12 and are supported using a hanger 76. Hanger 76 comprises a circular metallic band attached to the interior surface of wall sections 28 by stitchings circumferentially positioned around wall sections 28. Hanger 76 maintains the rigidity of the wall sections 28. Hanger 76 further includes reinforcing members 78 and 80 (FIG. 2A). Reinforcing members 78 and 80 serve to maintain the circular configuration of hanger 76 and also provide a point of attachment for the interior ends of the pelagic compartments 70 and trap 74. The interior ends of pelagic compartments 70 and trap 74 include a canvas tab 82 for attaching the interior ends of pelagic compartments 70 and trap 74 to the reinforcing members 78 and 80. This attachment maintains the pelagic compartments 70 and trap 74 in a substantially horizontal position within the interior of the conical-shaped enclosure 12.

The trap 74 is used to trap free swimming pelagic or demersal species located in the ambient waters surrounding the monitor 10. The zippered pelagic compartments 70 can be used to retain and separate benthic samples from fish swimming freely in the enclosure 12 and base portion 18. Although three zippered pelagic compartments 70 and one trap 74 have been illustrated in FIGS. 2 and 2A, any desired number of the zippered pelagic compartment 70 and trap 74 can be contained within the wall sections 28 of enclosure 12.

In operation, the monitor 10 is lowered to the sea floor using a cable (not shown) attached to the mounting plate 24. The weight of the base portion 18 serves as an anchor for the monitor 10 and stabilizes the monitor 10 on the sea floor. Additional weight for the base portion 18 may be provided by attaching exterior weights to the lower ends of the supporting rods 20 at the upper surface 22 of the base 18. An important aspect of the present invention is the shape of enclosure 12, the conical-shaped enclosure 12 is provided to reduce the effects of bottom currents present in the ambient waters surrounding the location to be studied. Once positioned, benthic samples can be placed within the receptacles 52 and zippered pelagic compartments 70 contained within the base portion 18 and enclosure 12. The water permeable wall sections 28 of enclosure 12 and water permeable vertical side walls 44, 46, 48 and 50 of base portion 18 of monitor 10 permit the free exchange of ambient water from outside the monitor 10 to within the enclosure 12 and base portion 18.

The benthic monitor 10 therefore, retains a benthic sample under study while allowing the sample to be exposed to continuous changes due to varying pollution occurring at the bottom of a body of water. The benthos under study may include, for example, crustaceans and free swimming pelagic or demersal fishes. The monitor 10 retains the benthos so that a sample that was exposed to the initial pollutant is still under study at the end of a test when exposed to a final pollutant. Furthermore, the monitor 10 acts as a trap for indigenous benthos which have been previously exposed to pollutants in the product environment under study.

The actual monitoring process utilizing the benthic monitor 10 may include several procedures. For example, a scientist may on a day-to-day basis or over a longer time interval collect subsamples of the benthic sample under investigation by sampling the contents of the receptacles 52 and the zippered pelagic compartments 70. The monitoring process may also include periodic retrieval of indigenous benthos which have entered the monitor 10 through traps 54 and 74 and which are retained within the monitor 10. Additionally, the benthic samples contained within the receptacles 52 and zippered pelagic compartments 70 can be replaced during the testing interval. During the testing period, in the event that the benthic sample required an additional food supply, such food can be pumped from a surface vessel using a hose that would enter the monitor 10 through the mounting plate 24. At the conclusion of the test, the benthic monitor 10 is removed from the water using, for example, a ship mounted crane to recoil the cable attached to the mounting plate 24 to lift the monitor 10 from the water.

The monitoring process utilizing the present invention can continue over extended periods of time so that the chronic impacts of various pollutants in the aquatic environment upon the benthic sample contained within the monitor 10 can be continuously observed. The monitor 10 permits the free exchange of ambient waters, while retaining a benthic sample to insure that the same sample has been continuously exposed to a changing aquatic environment. The monitor 10 is compartmentalized to afford protection of the various different species enclosed within the monitor 10 for observation.

Figure 4:
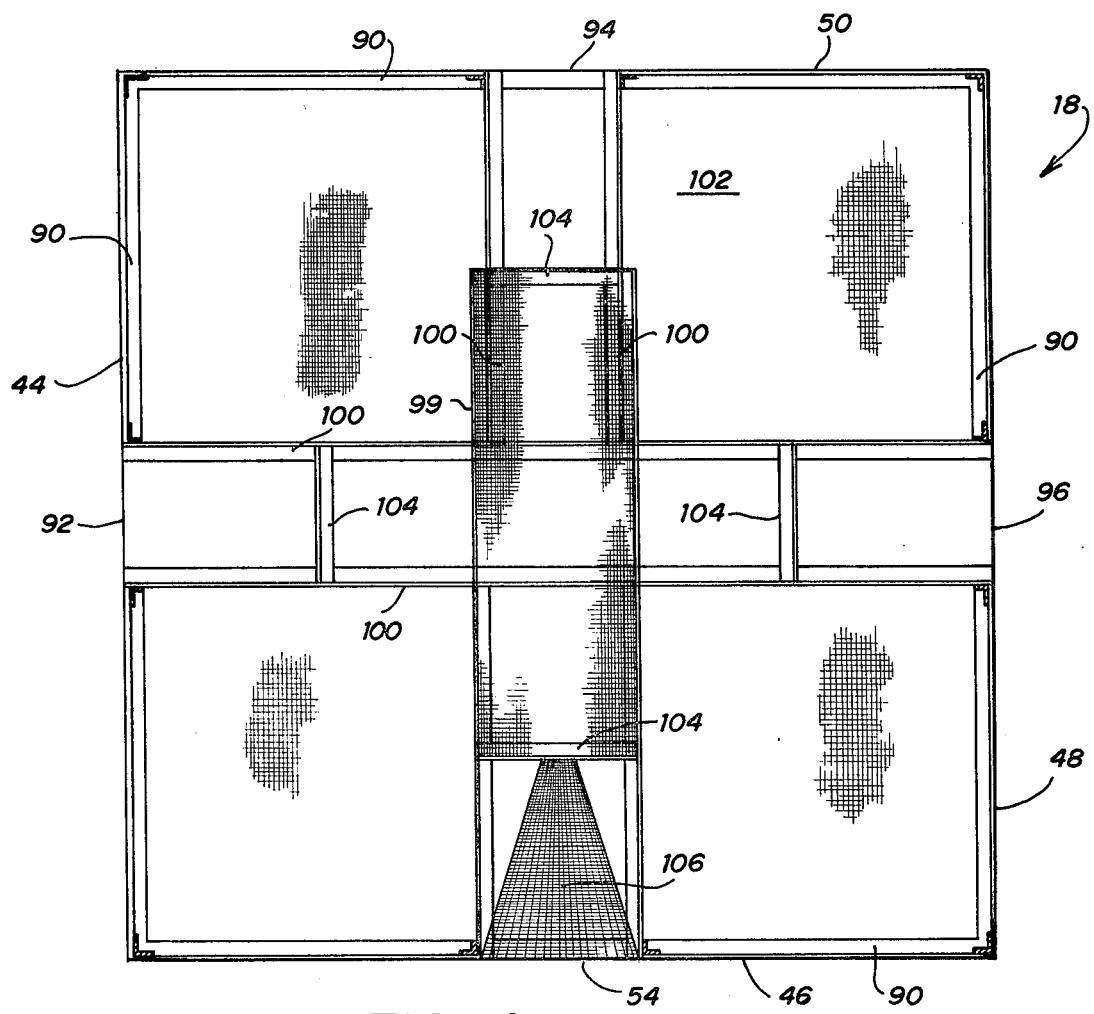
FIG. 4 is a sectional view taken generally along sectional lines 4—4 of FIG. 3.

Referring simultaneously to FIGS. 3, 4, 5 and 6, the base portion 18 of the monitor 10 is illustrated wherein like numerals are utilized for like and corresponding elements. The enclosure 12 has been removed from FIG. 3 for clarity of illustration. the base portion 18 includes rectangular frame members 90, which may be constructed of a non-toxic material such as stainless steel or aluminum. The vertical side walls 44, 48 and 50 include apertures 92, 94 and 96 for receiving receptacles 52. A partition 98 may be disposed between base portion 18 and enclosure 12 to divide the monitor 10 into separate subsections for isolating the benthic samples. Alternatively, an enclosure member 99 may be disposed between transverse frame members 104 between the trap 54 and the receptacle 52 opposite trap 54. Enclosure member 99 retains benthos which have entered the base portion 18 through trap 54 to prevent comingling with benthic samples contained within the enclosure 12. The enclosure member 99 may be constructed of a non-toxic mesh material such as stainless steel or aluminum and may be mechanically affixed to the transverse frame members 104 and the bottom 102 of base 18.

Receptacles 52 are slidable upon track members 100, which are disposed in the interior of base portion 18 along the bottom 102 thereof. Transverse frame members 104 provide support for the frame members 100 and a backstop for the receptacles 52. Bottom 102 of base portion 18 is water permeable and may comprise, for example, four mesh stainless steel wire. Trap 54 contained within the side wall 46 of base portion 18 includes a top wall 106 having edges conforming to edges of a triangular-shaped bottom wall 108.

Referring simultaneously to FIGS. 5 and 6, the trap 54 is more clearly illustrated. Trap 54 includes top wall 106 and bottom wall 108 which tapers upwardly from the bottom 102 of base portion 18. Trap 54 includes an entrance passage 110 to allow indigenous benthos to enter the monitor 10. The configurations of walls 106 and 108 forms an exit passage 112 opposite the entrance passage 110, but smaller in area to prevent the benthos from escaping the confines of monitor 10. Walls 106 and 108 of trap 54 comprise water permeable material, for example, 8 mesh stainless steel wire. While only one trap 54 is illustrated in FIGS. 3 through 6, any number of traps 54 and receptacles 52 can be utilized with the base portion 18 of monitor 10.

Referring simultaneously to FIGS. 6, 7 and 8, a spring latch 120 is illustrated for retaining receptacles 52 within the base portion 18 of monitor 10. Spring latch 120 is mounted on a transverse frame member 122 located in the side wall 48 of base portion 18. Latch 120 includes a mounting bracket 124 for attachment to the frame member 122. A rod 126 is disposed through the bracket 124 and includes a circumferentially mounted spring 128. At the lower end 126a of rod 126 and within the confines of mounting bracket 124 is a spring pin 130. Spring pin 130 is mounted through rod 126 and is operable to compress spring 128 such that lower end 126a of rod 126 is moved vertically upward to lower arm 124a of mounting bracket 124. When displaced upwardly, rod 126 permits receptacles 52 to be moved in and out of the side walls of base portion 18.

Referring to FIG. 9, receptacle 52 is illustrated. Receptacle 52 includes a lid 140, which is water permeable and may comprise, for example, 8 mesh stainless steel wire. Receptacle 52 includes side walls 142 and 144 and end walls 146 and 148. A bottom wall 150 is also provided for the receptacle 52. Walls 142, 144, 146, 148 and bottom wall 150 may be constructed of a water permeable mesh or may be solid in construction as illustrated in FIG. 9, depending upon the benthic samples being monitored. For example, if sediment and sediment-dwelling organisms are being studied, a receptacle 52 having solid walls would be utilized. Lid 140 is hingedly attached to end wall 148 using a hinge 151. Lid 140 further includes a latch 152. Latch 152 includes a member 154 having an aperture 156 for receiving rod 126 (FIG. 6) of the spring latch 120. Engagement of rod 126 with aperture 156 prevents the removal of receptacles 52 from the base portion 18 of monitor 10. Latch 152 further includes a member 158 having an aperture 160. When lid 140 is closed, aperture 160 aligns with an aperture 162 formed within end wall 146 to permit the lid 140 to be secured to the receptacle 52 using a pin 164.

It can thus be seen that the benthic aquatic biotal monitor of the present invention permits the detection of chronic impacts of various types of pollution in aquatic environments upon samples of benthos for extended periods of time. The monitor permits the free exchange of ambient water from outside the monitor enclosure and the inside of the enclosure wherein the benthic sample is retained. This free exchange of water permits the benthic sample to be continuously exposed to the ambient environment and changes to that environment. The monitor is structurally sound and lightweight to permit easy transportation to a test site and assembly at the test site.

It will also be seen that the monitor of the present invention retains a benthic sample to permit investigation and identity of the same benthic samples taken at the end of the exposure to the aquatic environment as that which had been exposed to the pollutant at the beginning of a test. The benthic monitor can also be utilized to study life cycles of organisms that are difficult to raise in a laboratory environment. Further, the monitor of the present invention can be utilized to conduct behavioral studies of various benthic organisms, explore mariculture at sea and study deep currents in the area using current meters attached to the base portion of the monitor.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. A benthic monitoring device for monitoring in situ samples of benthos in a body of water comprising:
   a base portion including means for retaining benthic samples and having a horizontal top wall, a horizontal water permeable bottom wall and water permeable vertical side walls,
   a water permeable mesh attached to and extending above said base portion to form a conical-shaped enclosure decreasing in cross-sectional area from one end to the other end, the larger end thereof being secured to said base portion and opening thereinto, the smaller end thereof being closed;
   means attached to said base portion for supporting said conical-shaped enclosure above said base portion;
   means for attaching said larger end of said conical-shaped enclosure to said base portion;
   said conical-shaped enclosure including means for retaining benthic samples; and
   said conical-shaped enclosure and said base portion having apertures therethrough with dimensions for retaining benthic samples while permitting the free exchange of ambient water between the outside of said conical-shaped enclosure and the inside of said conical-shaped enclosure to monitor the impact of changing aquatic environments on the benthic sample.

2. The monitoring device of claim 1 wherein said water permeable mesh includes means projecting into said conical-shaped enclosure for retaining benthic samples therein.

3. The monitoring device of claim 2 wherein said water permeable mesh further includes at least one entry passage projecting into said conical-shaped enclosure for trapping within the monitoring device benthic organisms found in the ambient water outside of said monitoring device.

4. The monitoring device of claim 3 wherein said water permeable mesh further includes access means for removing benthic samples from the monitoring device without removing said conical-shaped enclosure from said base portion.

5. The monitoring device of claim 1 wherein said base portion further includes at least one entry passage for allowing benthic organisms found in ambient water outside of the monitoring device to enter said base portion.

6. The monitoring device of claim 5 wherein said base portion further includes a trap, aligned with said entry passage and extending inwardly into said base portion from said entry passage.

7. The monitoring device of claim 6 wherein said trap includes:
   a substantially horizontal, triangular-shaped bottom wall tapering upwardly into said base portion;
   a top wall portion having edges conforming to said trap bottom wall portion; and
   an exit passage disposed opposite said entry passage being smaller in area than said entry passageway to prevent the benthic organisms from escaping the confines of said monitoring device.

8. The monitoring device of claim 7 wherein said means for retaining benthic samples comprises a plurality of drawer means for insertion into said base portion through said vertical side walls and including top, bottom, side and end members.

9. The monitoring device of claim 8 wherein each of said drawer means top members comprises a water permeable mesh.

10. The monitoring device of claim 8 wherein ones of said plurality of drawer means bottom, side and end members comprise water permeable mesh walls.

11. The monitoring device of claim 8 wherein ones of said plurality of drawer means bottom, side and end members comprise solid walls.

12. A benthic monitoring device for monitoring in situ samples of benthos in a body of water comprising:
a base portion having water permeable vertical side walls and horizontal top and bottom walls, said vertical side walls including apertures for receiving means for retaining benthic samples, at least one of said vertical side walls further including an entry passage for allowing benthic organisms found in ambient water outside of the monitoring device to enter said base portion;
a water permeable mesh attached to and extending above said base portion to form a conical-shaped enclosure decreasing in cross-sectional area from one end to the other end, the larger end thereof being secured to said base portion and opening thereinto, the smaller end thereof being closed;
said conical-shaped enclosure including means for retaining benthic samples;
means for supporting said conical-shaped enclosure above said base portion;
means for attaching said larger end of said conical-shaped enclosure to said base portion; and
said conical-shaped enclosure and said base portion having apertures therethrough with dimensions for retaining benthic samples therein, while permitting the free exchange of ambient water between the outside of said conical-shaped enclosure and the inside of said conical-shaped enclosure to thereby expose the samples of benthos to aquatic pollution within the body of water to monitor the impact of changing aquatic environments on the benthic samples.

13. The monitoring device of claim 12 wherein said conical-shaped enclosure further includes:
a plurality of cylindrical compartments projecting into said conical-shaped enclosure for retaining benthic samples; and
at least one entry passage projecting into said conical-shaped enclosure for trapping within the monitoring device benthic organisms found in ambient water outside of the monitoring device.

14. The monitoring device of claim 13 wherein said base portion further includes:
a trap, aligned with said base entry passage and extending inwardly into said base portion from said entry passage;
said trap including a substantially horizontal, triangular-shaped bottom wall tapering upwardly into said base portion;
a top wall portion having edges conforming to said trap bottom wall portion; and
an exit passageway disposed opposite said entry passage being smaller in area than said entry passage to prevent the benthic organisms from escaping the confines of said monitoring device.

15. The monitoring device of claim 12 wherein said water permeable mesh comprises nylon netting having apertures sized from about 2 millimeters to about 3 millimeters.

16. The monitoring device of claim 12 wherein said means for attaching said larger end of said conical-shaped enclosure to said base portion includes:
a circular webbing attached to said larger end of said conical-shaped enclosure;
a circular flange extension mounted to said top wall of said base portion; and
a flexible metallic band for mounting said circular webbing to said circular flange extension, such that said conical-shaped enclosure and said base portion form a unitary structure.

17. The monitoring device of claim 16 and further including partition means for preventing benthic samples from moving between said conical-shaped enclosure and said base portion.

* * * * *